United States Patent [19]

Czuppon

[11] Patent Number: 5,223,238
[45] Date of Patent: Jun. 29, 1993

[54] METHOD FOR TREATING AMMONIA AND UREA CONDENSATES

[75] Inventor: Thomas A. Czuppon, Houston, Tex.

[73] Assignee: The M. W. Kellogg Company, Houston, Tex.

[21] Appl. No.: 821,209

[22] Filed: Jan. 16, 1992

[51] Int. Cl.$^5$ .................... C01C 1/04; C07C 273/00
[52] U.S. Cl. .................................. 423/359; 564/69; 564/73
[58] Field of Search .................. 423/359; 564/69, 70, 564/71, 72, 73

[56] References Cited

U.S. PATENT DOCUMENTS 3,970,739 7/1976 Shiraishi et al. .
4,341,640 7/1982 Landis .
4,410,503 10/1983 Van Nassau et al. .
4,552,979 11/1985 Stokes .

Primary Examiner—Wayne Langel
Attorney, Agent, or Firm—John P. Ward

[57] ABSTRACT

A method is described which enables ammonia plant process condensate contaminated with ammonia, carbon dioxide and methanol and urea plant condensate contaminated with urea, ammonia, carbon dioxide and other combined forms of ammonia and carbon dioxide to be simultaneously converted, in a single treatment vessel, substantially and continuously to a vaporous stream rich in ammonia, carbon dioxide and methanol and an liquid stream poor in ammonia, carbon dioxide, methanol and urea. The vaporous stream thus produced is recycled and employed as a feedstock in the reforming section in the ammonia plant.

9 Claims, 1 Drawing Sheet

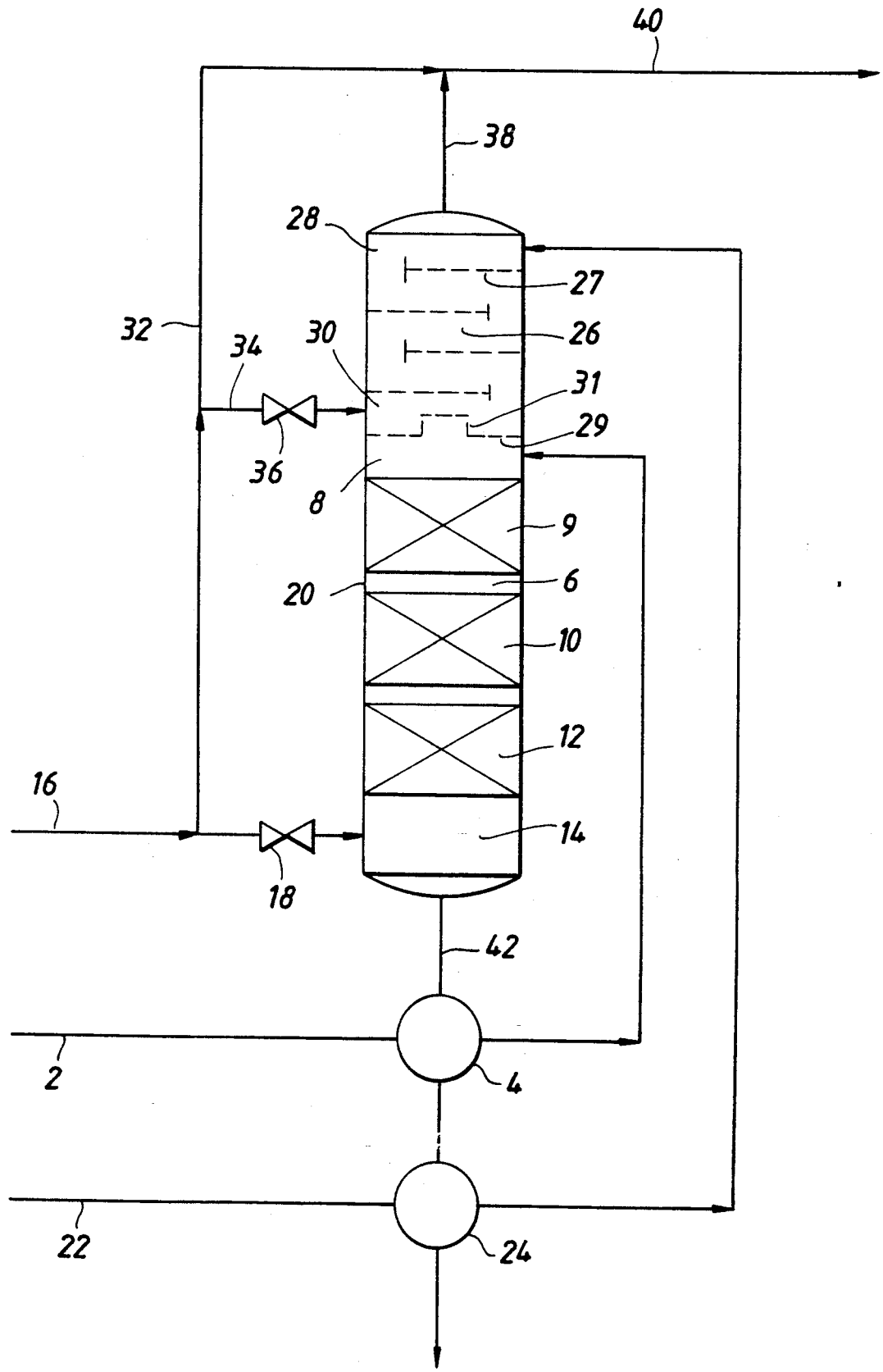

METHOD FOR TREATING AMMONIA AND UREA CONDENSATES

FIELD OF THE INVENTION

The present invention relates to a method for the simultaneous treatment of the individual by-product condensate streams produced in and recovered from a facility, wherein both ammonia and urea are manufactured. More particularly, the present invention relates to a method for simultaneously hydrolyzing and stripping such by-product process condensate streams in a single treatment vessel to produce a single vaporous product stream rich in ammonia, methanol and carbon dioxide values and a single liquid product stream poor in such values.

BACKGROUND OF THE INVENTION

It is known that in the manufacture of ammonia and urea, large quantities of by-product process condensates are produced. In the manufacture of urea, for example, one mole of by-product water is formed for each mole of urea produced. When this by-product water is considered together with other water used and/or produced in a urea process, the total amount of process condensate and such other water combined can range from 40 to 60 percent by weight of the total weight of the urea being produced. Similarly, in the manufacture of ammonia, the amount of process by-product condensate produced typically can range from 100 to 135 percent by weight of the total weight of the ammonia being produced.

Unfortunately, the by-product process condensates produced in and recovered from such ammonia and urea manufacturing facilities contain contaminants of such a nature that typically they cannot be readily recycled for reuse in the manufacturing processes or discarded to the environment. Generally, contaminants found in the process condensates produced in and recovered from the manufacture of urea can contain not only from 1.0 to 1.5 percent by weight of urea but also from 4 to 8 percent by weight of ammonia and from 2.0 to 5.5 percent by weight of carbon dioxide. The process condensates produced in and recovered from the manufacture of ammonia typically can contain from 0.05 to 0.1 percent by weight of ammonia, from 0.2 to 0.3 percent by weight of carbon dioxide and from 0.05 to 0.2 percent by weight of methanol and, in addition thereto traces of higher alcohols, amines and other hydrocarbon components.

To render the above by-product process condensates useful for recycle in the manufacturing process or readily disposable to the environment, it has been common practice to subject these process condensates to some form of treatment to remove as much of the aforementioned contaminants as possible. Thus, for example, U.S. Pat. No. 4,552,979 describes a continuous process for the treatment of urea plant process condensate containing urea values utilizing both steam and a hydrocarbon fuel gas to hydrolyze the urea values and to strip ammonia and carbon dioxide from the hydrolyzed condensate. The water present in the condensate is converted into steam for use in the process. As an end-product of the process, a gaseous stream comprised of steam, hydrocarbon fuel gas, ammonia and carbon dioxide is recovered which, if the urea plant contains as an integral part thereof an ammonia plant reformer, can be used as a feedstock to such reformer. U.S. Pat. No. 4,341,640 describes an improvement in the treatment of urea plant process condensates requiring the use of a vessel having at least one treating cell comprising an inner cylinder located within the vessel having inside and outside surfaces, and one or more stripping trays connected to the inner surface and a liquid holding zone located between the outer surface of the cylinder and the vessel. This zone is maintained substantially separate from the vapor streams passing through the vessel.

Processes for the treatment of by-product process condensates produced during ammonia manufacture are exemplified by U.S. Pat. No. 3,970,739. This patent describes a process for concurrently treating process waste waters and flue gases from ammonia synthesis process plants. The process involves stripping ammonia and organic materials, as gases, from the process waste water and decomposing the methanol contained in the stripped gas over a first catalyst suited for decomposing methanol to produce a gas containing carbon dioxide and water or carbon dioxide, water and hydrogen. The resulting gas, further containing undecomposed ammonia is mixed with the flue gases from the ammonia plant and the gaseous mixture brought into contact with a second catalyst capable of reducing the nitrogen oxides contained in said gaseous mixture to nitrogen and water. Finally the resulting gaseous mixture is contacted with a third and final catalyst capable of decomposing any unreacted ammonia by oxidation into nitrogen and water.

Exemplary of processes for the removal of urea, ammonia and carbon dioxide from process condensates derived from a coupled ammonia and urea synthesis process is U.S. Pat. No. 4,410,503. This patent describes an improved process where the process condensate resulting from the urea synthesis first is treated in a desorption or stripping column to remove as much of the ammonia and carbon dioxide contained therein as possible and to render said condensate poor with respect to ammonia. Thereafter the ammonia-poor process condensate is introduced into a separate reaction column along with process condensate resulting from the ammonia synthesis and the combined condensates treated with steam. A gas mixture rich in ammonia, carbon dioxide and water vapor is removed from the top of the reaction column and an aqueous liquid poor in said urea, ammonia and carbon dioxide is removed from the bottom of the reaction column. The disadvantage of this process is the need to first treat the process condensate from the urea synthesis prior to combining said condensate, now poor with respect to ammonia, with the process condensate from the ammonia synthesis within the separate reaction column. The need for this separate, first treatment step results in a significant increase in capital costs for equipment required to carry out this first treatment step.

An objective of the present invention is to provide an improved process for treating the by-product process condensates produced and recovered from facilities wherein both ammonia and urea are manufactured. It is a further objective to provide an improved process for the simultaneous treatment of such by-product process condensates in a single treatment vessel thereby reducing the additional capital costs associated with the additional equipment required for the process described in U.S. Pat. No. 4,410,503.

SUMMARY OF THE INVENTION

According to the present invention, in a facility for synthesizing both ammonia and urea wherein first and second by-product process condensates are produced, there is provided a continuous method for simultaneously treating said process condensates in a single, vertically positioned treatment vessel having an upper hydrolysis zone and a lower stripping zone. The method of the present invention comprises preheating the first process condensate produced in an ammonia synthesis process and comprising a dilute aqueous stream consisting essentially of water, ammonia, carbon dioxide, methanol and traces of higher alcohols, amines and other hydrocarbon components and introducing the preheated first process condensate into an upper end of the stripping zone. Within the upper end of the stripping zone, the preheated first process condensate is blended with a first liquid stream, poor in urea values, collected in and withdrawn from a lower end of the upper hydrolysis zone which is in fluid communication with the upper end of the lower stripping zone. The resulting blended stream then is contacted in a countercurrent flow relationship with steam introduced into a lower end of the stripping zone. This contact is carried out under temperature and pressure conditions effective to strip a substantial portion of the ammonia, carbon dioxide and methanol values contained in the blended stream and to produce a vaporous stream rich in ammonia, carbon dioxide and methanol values and further containing the traces of higher alcohols, amines and other hydrocarbon components and a second liquid stream poor in said ammonia, carbon dioxide and methanol values. The vaporous stream is withdrawn from the upper end of the stripping zone and introduced into the lower end of the hydrolysis zone, with which it is in fluid communication, of the treatment vessel.

The second process condensate stream, which comprises a dilute aqueous stream consisting essentially of water, urea, ammonia and carbon dioxide, also is preheated and introduced into an upper end of the hydrolysis zone of the treatment vessel. Within the hydrolysis zone, this second process condensate is further heated by contacting said second process condensate stream in a countercurrent flow relationship with the vaporous stream withdrawn from the upper end of the stripping zone and introduced into the lower end of the hydrolysis zone and, optionally, fresh process steam also introduced into the lower end of the hydrolysis zone. The contact between the preheated second process condensate stream and the vaporous stream and, optionally, the fresh process steam introduced into the lower end of the hydrolysis zone is carried out under temperature and pressure conditions effective to substantially hydrolyze the urea present in the second process condensate to ammonia and carbon dioxide and to produce the first liquid stream which is poor in urea values and rich in ammonia and carbon dioxide values. The first liquid stream which collects in the lower end of the hydrolysis zone is passed therefrom into the upper end of the stripping zone.

Finally, the vaporous stream is withdrawn from the hydrolysis zone through the upper end thereof while the second liquid stream, substantially free of ammonia, carbon dioxide and methanol values is withdrawn from the stripping zone of the treatment vessel through the lower end thereof.

In a further embodiment of the present invention, the vaporous stream withdrawn from the hydrolysis zone is conveyed to and utilized in the reforming stage of the ammonia synthesis section of the ammonia and urea manufacturing facility. In yet a further embodiment of the present invention, the second liquid stream can be utilized to preheat both the ammonia synthesis and urea synthesis process condensates by passing said respective process condensates in heat exchange relationship with said effluent stream.

DESCRIPTION OF THE DRAWING

The single FIGURE represents a simple flow diagram illustrating the practice of the present invention in concurrently treating process condensates produced in facilities wherein both ammonia and urea are manufactured.

DETAILED DESCRIPTION OF THE INVENTION

Referring to the single FIGURE, an ammonia synthesis process condensate, produced in a facility for the manufacture of both ammonia and urea, is conveyed at an elevated pressure in the range from about 3.8 MPa to about 7.5 MPa by way of conduit 2 and through heat exchanger 4, wherein it is preheated to a temperature in the range from about 220° C. to about 285° C., to treatment vessel 20. Treatment vessel 20 is provided with a lower stripping zone 6 having an upper end 8 and a lower end 14 and an upper hydrolysis zone 26 having an upper end 28 and a lower end 30. In the single Figure, lower stripping zone 6 further is provided with multiple liquid/vapor contact sections 9, 10 and 12 which may comprise, for example, packed sections utilizing any of the known "dumped" or "arranged" packing materials. Representative, but non-limiting, examples of dumped packing materials include Berl saddles, Intalox saddles, Pall rings and the like while representative, but non-limiting, examples of arranged packings include Flexipak, Hyperfil and Kloss packings and the like. Descriptions and/or illustrations of both types of packing materials can be found in *Perry's Chemical Engineers Handbook*, 6th Ed., (1984), Section 18, pp. 19-26.

The preheated ammonia synthesis process condensate flowing in conduit 2 is introduced into stripping zone 6 of treatment vessel 20 at upper end 8 thereof. Upon entering upper end 8 of stripping zone 6, the process condensate stream is blended with a first liquid stream poor in urea values and rich in ammonia and carbon dioxide values being collected in and withdrawn from lower end 30 of the upper hydrolysis zone 26. The resulting blended stream then is flowed downwardly through stripping zone 6 and contact sections 9, 10 and 12 provided therein where it is intimately contacted with process steam flowing upwardly through stripping zone 6 and contact sections 9, 10 and 12. The process steam is introduced into stripping zone 6 at lower end 14 by way of steam conduit 16 and valve 18 under a pressure within the range mentioned above for the ammonia synthesis process condensate, i.e., a pressure within the range from about 3.8 MPa to about 7.5 MPa. This process steam is introduced into stripping zone 6 at lower end 14 at a rate sufficient to provide a weight ratio of process steam to the total process condensate streams being introduced into treatment vessel 20 ranging from about 0.4 to about 0.6.

From lower section 14, the process steam flows upwardly through stripping zone 6 and contact sections 9, 10 and 12 whereby the ammonia, carbon dioxide, methanol and other hydrocarbon components contained in said blended stream substantially are stripped therefrom and entrained in the process steam to form a vaporous stream rich in ammonia, carbon dioxide and methanol values and further containing the traces of higher alcohols, amines and other hydrocarbon components. The stripped blended stream or second liquid stream contains substantially reduced levels of ammonia and methanol and substantially no carbon dioxide. The second liquid stream is collected in lower end 14 of stripping zone 6. This second liquid stream is removed from lower end 14 of stripping zone 6 through conduit 42. The heat energy contained in this stripped blended stream or second liquid stream is utilized to preheat the ammonia synthesis process condensate being fed to the stripping zone 6 of treatment vessel 20 and thus may be passed in heat exchange relationship with the latter condensate within heat exchanger 4.

Concurrently with the treatment of the blended stream of the first liquid stream and the ammonia synthesis process condensate within stripping zone 6 of treatment vessel 20, the urea synthesis process condensate is subjected to hydrolysis in treatment vessel 20 in hydrolysis zone 26 provided therein. Returning to the single Figure, the urea synthesis process condensate stream is conveyed at an elevated pressure within the range from about 3.8 MPa to about 7.5 MPa by way of conduit 22 and through heat exchanger 24 and introduced into hydrolysis zone 26 at upper end 28 thereof. Depending upon the concentrations of the ammonia and carbon dioxide contained in the urea synthesis process condensate in conduit 22, it may be desireable to subject this process condensate to a fractionation step (by means not shown) to remove at least a portion of the ammonia and carbon dioxide therefrom prior to the introduction of this process condensate into hydrolysis zone 26. The ammonia and carbon dioxide thus removed can be conveyed to the urea synthesis section of the ammonia and urea manufacturing facility. From upper end 28 the urea synthesis process condensate, preheated within heat exchanger 24 to a temperature in the range of from about 130° C. to about 195° C., flows downwardly through hydrolysis zone 26 which is provided with multiple liquid and vapor contact trays 27. Upon the multiple liquid and vapor contact trays 27, the downwardly flowing preheated urea synthesis process condensate is intimately contacted with the upwardly flowing vaporous stream produced in and withdrawn from the stripping zone 6 via upper end 8 thereof.

In a further embodiment of the present invention, the vaporous stream may be combined with fresh process steam and the resulting mixture contacted in a countercurrent flow relationship with said urea synthesis process condensate. In this embodiment, the fresh process steam is introduced into hydrolysis zone 26 at lower end 30 provided therein by way of conduits 16, 32 and 34 and valve 36 under a pressure within the range mentioned above for the urea synthesis process condensate, i.e., from about 3.8 MPa to about 7.5 MPa. When utilized, this fresh process steam is introduced into hydrolysis zone 26 at lower end 30 at a rate sufficient to provide a weight ratio of fresh process steam to the urea synthesis process condensate being fed to hydrolysis zone 26 up about 0.2.

From lower end 30, the vaporous stream and, optionally, the fresh process steam flow upwardly through hydrolysis zone 26 and multiple contact trays 27 provided therein whereby the urea contained in the urea synthesis process condensate is intimately contacted with the vaporous stream and, optionally, the fresh process steam and substantially converted to ammonia and carbon dioxide. Typically the rates of flow of the urea synthesis process condensate and the vaporous stream countercurrently through the hydrolysis zone 26 are adjusted so as to provide a contact time between the condensate stream and the first vaporous stream of between about 1 and 5 minutes. The ammonia and carbon dioxide produced by hydrolysis of the urea synthesis process condensate are essentially contained in the liquid stream, i.e., the first liquid stream, being produced during the hydrolysis of this condensate stream. The liquid stream is collected in lower end 30 of hydrolysis zone 26. The ammonia and carbon dioxide values contained in this liquid stream are subsequently stripped therefrom in stripping zone 6.

The vaporous stream produced in stripping zone 6 and passed through hydrolysis zone 26 in countercurrent flow relationship to the urea synthesis process condensate is removed from treatment vessel 20 via upper end 28 of hydrolysis zone 26 through conduits 38 and 40. This vaporous stream is suitable for use in production of further synthesis gas for use in the ammonia synthesis section of the ammonia and urea manufacturing facility and thus can be conveyed through conduit 40 directly to the steam reforming section (not shown) of the ammonia synthesis section of such facility.

To further illustrate the practice of the method constituting the present invention in accordance with the flow diagram shown in the single Figure, process condensates obtained from a facility for the manufacture of both ammonia and urea are treated in the manner described below. Unless specified otherwise, all quantities are expressed in parts or parts/hour.

A process condensate recovered from the ammonia synthesis section of a facility for the manufacture of both ammonia and urea is flowed continuously through conduit 2 at a rate of 57,297 parts/hour. This condensate contains 172 parts of carbon dioxide, 57 parts of ammonia, 57 parts of methanol and 57,011 parts of water and is recovered from the facility under a pressure of about 4.2 MPa and at a temperature of about 93° C. This process condensate is heated in heat exchanger 4 to a temperature of about 241° C. and introduced into the stripping zone 6 of treatment vessel 20 at upper end 8. Therein it is blended with a first liquid stream poor in urea values and rich in ammonia and carbon dioxide values, said first liquid stream being produced in hydrolysis zone 26 of treatment vessel 20. The resulting blended stream flows downwardly through stripping zone 6 containing multiple liquid/vapor contact sections 9, 10, and 12 wherein it is contacted in a countercurrent flow relationship with 36,056 parts of process steam introduced into stripping zone 6 at lower end 14 through conduit 16 and valve 18. This process steam is continuously introduced into stripping zone 6 at a temperature of about 374° C. and a pressure of about 4.2 MPa to produce a vaporous stream containing substantially all of the ammonia, carbon dioxide and methanol present in the process condensate from the ammonia synthesis section of the facility and the ammonia and carbon dioxide contained in the first liquid stream.

Concurrently with the stripping of the blended stream of the process condensate from the ammonia synthesis section of the facility and the first liquid stream, the process condensate from the urea synthesis section of the ammonia and urea manufacturing facility is flowed continuously through conduit 22 at a rate of 29,189 parts/hour. This condensate contains 282 parts of urea, 553 parts of carbon dioxide, 1,278 parts of ammonia and 27,076 parts of water and is recovered from the facility under a pressure of about 4.2 MPa. This process condensate is preheated in heat exchanger 24 from an initial temperature of about 56° C. to a temperature of about 152° C. The preheated process condensate then is introduced into hydrolysis zone 26 of treatment vessel 20 at upper end 28. From upper end 28, the preheated process condensate flows downwardly through hydrolysis zone 26 where, in a preferred embodiment, it is intimately contacted in a countercurrent flow relationship with a vaporous mixture comprised of optional fresh process steam and the vaporous stream produced in stripping zone 6 of treatment vessel 20. This vaporous mixture is formed by introducing the optional fresh process steam at a temperature of about 374° C. and under a pressure of about 4.2 MPa and the first vaporous stream produced in stripper zone 6 into lower end 28 wherein it is combined and is flowed upwardly through hydrolysis zone 26. The optional fresh process steam is introduced into lower end 30 via conduits 16, 32 and 34 and valve 36 while the vaporous stream is passed directly from upper end 8 of stripping zone 6 to lower end 30 of hydrolysis zone 26 which are in direct fluid communication via passageway or riser 31 located in tray 29.

Within hydrolysis zone 26, the urea present in the process condensate from the urea synthesis section is substantially hydrolyzed to ammonia and carbon dioxide. The ammonia and carbon dioxide contained in the first liquid stream resulting from the hydrolysis of the urea containing process condensate are subsequently stripped therefrom in stripping zone 6 of treatment vessel 20. The first vaporous stream, which is continuously withdrawn from hydrolysis zone 26 at upper end 28 via conduit 38 at a rate of 36,410 parts/hour contains 1492 parts of ammonia, 932 parts of carbon dioxide and 53 parts of methanol. In a preferred embodiment of the present invention as illustrated in the single Figure, this vaporous stream is combined with the balance of the process steam flowing through conduit 32 and the resulting mixed stream conveyed to the steam reforming section of the ammonia synthesis section of the ammonia and urea manufacturing facility (both not shown).

While the present invention has been described with respect to what at present is considered to be the preferred embodiments thereof, it is to be understood that modifications and changes can be made thereto without departing from the spirit and scope of the invention as described above and as defined in the following claims.

What is claimed is:

1. In a process for manufacturing both ammonia and urea wherein first and second process condensates are produced, a continuous method for concurrently treating said process condensates in a single, vertically positioned treatment vessel having an upper hydrolysis zone and a lower stripping zone comprising the steps of:
   (a) preheating the first process condensate comprising a dilute aqueous stream consisting essentially of ammonia, carbon dioxide and methanol and introducing said preheated first condensate into an upper end of the lower stripping zone of the single treatment vessel;
   (b) blending the preheated first condensate within the upper end of the stripping zone with a first liquid stream produced in and recovered from the upper hydrolysis zone of the single treatment vessel;
   (c) contacting the blended stream, within the stripping zone, in a countercurrent flow relationship with steam introduced into a lower end of the stripping zone, said contact being carried out at a temperature and pressure effective to remove a substantial portion of the ammonia, carbon dioxide and methanol from said blended stream and thereby produce an aqueous vaporous stream rich in said ammonia, carbon dioxide and methanol and a second liquid stream substantially free of said ammonia, carbon dioxide and methanol;
   (d) withdrawing the vaporous stream from the upper end of the stripping zone and introducing the vaporous stream into a lower end of the upper hydrolysis zone of the single treatment vessel;
   (e) preheating the second process condensate comprising a dilute aqueous stream consisting essentially of water, urea, ammonia and carbon dioxide and introducing said preheated second condensate into an upper end of the hydrolysis zone of the single treatment vessel;
   (f) contacting the preheated second condensate, within the hydrolysis zone, in a countercurrent flow relationship with the vaporous stream produced in and withdrawn from the lower stripping zone, said contact being carried out at a temperature and pressure effective to hydrolyze the urea contained in the preheated second condensate to ammonia and carbon dioxide and thereby produce the first liquid stream rich in said ammonia and carbon dioxide;
   (g) withdrawing said vaporous stream from said hydrolysis zone and the second stream from said stripping zone.

2. The method of claim 1 further comprising the step of recycling said vaporous stream enriched in said ammonia, carbon dioxide and methanol to a steam reforming stage for producing an ammonia synthesis gas for use in ammonia manufacture.

3. The method of claim 1 wherein said first process condensate is provided under a pressure in the range of from about 3.8 MPa to about 7.5 MPa and wherein said first condensate is preheated to a temperature in the range from about 220° C. to about 285° C.

4. The method of claim 1 wherein the second process condensate is provided under a pressure in the range from about 3.8 MPa to about 7.5 MPa and is preheated to a temperature in the range from about 130° C. to about 195° C.

5. The method of claim 1 wherein said contact of said blended stream with said steam in said stripping zone is carried out at a weight ratio of steam to total process condensates being treated in said treatment vessel ranging from about 0.4 to about 0.6.

6. The method of claim 1 wherein said contact between the preheated second condensate and said vaporous stream in said hydrolysis zone is maintained for a period of time ranging from about one to about five minutes.

7. The method of claim 6 wherein said contact further is carried out in the presence of added steam.

8. The method of claim 1 wherein the first and second process condensates are preheated by indirect heat exchange with said second liquid stream withdrawn from the lower end of said stripping zone.

9. The method of claim 1 wherein the second stream withdrawn from the lower end of the stripping zone contains urea and ammonia concentrations of 5 ppm and less respectively and a methanol concentration of 25 ppm and less.

* * * * *